United States Patent [19]
Friedrich et al.

[11] Patent Number: 6,166,207
[45] Date of Patent: Dec. 26, 2000

[54] PREPARATION OF BICYCLIC AMIDINES AND DIAZACYCLOALKENES

[75] Inventors: Wolfgang Friedrich, Speyer; Heinz-Josef Kneuper, Mannheim; Karsten Eller; Tom Witzel, both of Ludwigshafen, all of Germany

[73] Assignee: BASF Aktiengesellschaft, Ludwigshafen, Germany

[21] Appl. No.: 09/201,083

[22] Filed: Nov. 30, 1998

[30] Foreign Application Priority Data

Nov. 28, 1997 [DE] Germany .................. 197 52 935

[51] Int. Cl.⁷ .................................. C07D 239/00
[52] U.S. Cl. ..................... 544/282; 544/253; 544/242
[58] Field of Search .................. 544/245, 282, 544/242, 253

[56] References Cited

U.S. PATENT DOCUMENTS 3,761,436  9/1973  Hashimoto et al. .............. 252/431
5,723,605  3/1998  Werbitzky et al. ............... 540/567

FOREIGN PATENT DOCUMENTS 662476  12/1995  European Pat. Off. .

OTHER PUBLICATIONS

Oediger et al., *Synthesis*, 1972, pp. 591–598.
Oediger et al., *Chem. Ber.*, 99, 1966, pp. 2012–2016.
Xing–Quan, *J. Nat. Gas Chem.*, 4, 1995, pp. 119–127.
Nakatani et al., *Chem. Expr.*, vol. 8, 1993, pp. 825–828.
Lin et al., *Proc. SPI Annu. Tech./Mark. Conf.*, 1984, pp. 138–141.
Lagerman et al., *J. Am. Oil Chem. Soc.*, 71, 1994, pp. 97–100.
Oediger at al., 1.5–Diaza–bicyclo(4.3.0)nonen–(5); "Chem.Ber."99,2012–16(Jan. 1966).

*Primary Examiner*—Mukund J. Shah
*Assistant Examiner*—Sudhaker B. Patel
*Attorney, Agent, or Firm*—Keil & Weinkauf

[57] ABSTRACT

In a process for preparing a bicyclic amidine by reacting a lactone and a diamine with elimination of water, water formed by elimination is removed from the reaction mixture during the reaction. A diazabicycloalkene, a process for its preparation and its use are also described.

8 Claims, No Drawings

PREPARATION OF BICYCLIC AMIDINES AND DIAZACYCLOALKENES

The present invention relates to a process for preparing a bicyclic amidine during which a diazacycoalkene is formed as an intermediate. The invention also relates to a diazacycoalkene, to a process for its preparation and to its use for preparing a bicyclic amidine.

Bicyclic amidines, in particular diazabicyloalkenes, are frequently used as strong bases in organic chemical reactions. Thus, these compounds originally became known because of their ability to aid dehydrohalogenation reaction, which was first employed in the synthesis of vitamin A. However, bicyclic amidines can also be used in other reactions, frequently resulting in milder reaction conditions than when conventional bases are used, a higher selectivity and frequently also a higher yield.

Bicyclic amidines can be prepared by various methods. One known synthetic route first proceeds via the addition of acrylonitrile onto a lactam, forming a cyanoethyl-lactam. This lactam is subsequently hydrogenated to form the aminopropyl-lactam and, in a final step, cyclized in the presence of an acid catalyst and with elimination of water to form the bicyclic amidine (Oedinger et al., Synthesis (1972), pp. 591–598; idem, Chem. Ber. 99 (1966) pp. 2012–2016 and Xing-Quan, J. Nat. Gas Chem. 4 (1995) pp. 119–127). Disadvantages of this process are the number of stages involved and the necessity of using the highly toxic acrylonitrile as reagent.

However, the use of acrylonitrile can be avoided by a two-stage preparation of the bicyclic amidine starting from lactones. DE-C 730 182 describes the preparation of aminoalkylpyrrolidones starting from lactones and diamines by heating for a number of hours in an autoclave. The product thus obtained can then, using a method similar to that described above, be cyclized in the presence of an acid catalyst (e.g. as described in DE-C 1 545 855) to give a bicyclic amidine.

EP-A 0 662 476 combines these two steps and discloses a process for preparing bicyclic amidines by heating lactones and diamines with addition of an acid catalyst in an autoclave. A disadvantage is the need to work under superatmospheric pressure. This requires expensive pressure vessels which also, owing to the acid catalyst which is necessary in the process disclosed, have to be made of specific acid-resistant materials. An analogous process is described by Nakatani et al. in Chem. Expr. 8 (1993) pp. 825–828.

DE-A 35 12 627 describes the reaction of lactones such as butyrolactone with amines such as 1,3-diaminopropane and acids such as oxalic acid to give open-chain amide salts such as 3-(4-hydroxybutanoylamino)propylammonium oxalate. Lin and Gromelski (Proc. SPI Annu. Tech./Mark. Conf (1984), pp. 138–141) likewise describe the preparation of open-chain amides of the type N,N'-(1,ω-alkylene)bis-4-hydroxybutyramide in the reaction of butyrolactone with diamines; the amides cyclize at elevated temperatures to form alkylenebispyrrolidones. Lagerman et al. (J. Am. Oil Chem. Soc. 71 (1994), pp. 97–100) describe the formation of open-chain amides in the reaction of diamines having a primary and a secondary amino group with butyrolactone or caprolactone.

EP-A 0 382 056 describes the reaction of lactams with diamines in the gas phase over zeolites at elevated temperatures and atmospheric pressure. However, the yields of bicyclic amidines which could be achieved are unsatisfactory and the document gives no information about the operating life of the zeolite catalysts.

It is an object of the present invention to provide a process for preparing a bicyclic amidine which makes do without the costly use of pressure vessels, in which use of acid catalysts is not necessary and which leads to the desired bicyclic amidine in high yields.

We have found that this object is achieved by reacting a lactone and a diamine with removal of the water of reaction during the course of the reaction to form the bicyclic amidine.

The present invention accordingly provides a process for preparing a bicyclic amidine of the formula I

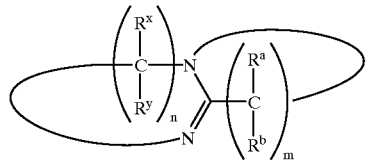

(I)

where $R^x$, $R^y$, $R^a$ and $R^b$ are each, independently of one another, hydrogen, $C_1$–$C_{10}$-alkyl, $C_2$–$C_{10}$-alkenyl, $C_2$–$C_{10}$-alkynyl or $C_6$–$C_{12}$-aryl, where the radicals can in turn be further substituted by hydroxy, amino, $C_1$–$C_4$-alkylamino or mercapto groups, and n and m are, independently of one another, numbers from 2 to 12, where a, b, x and y each index the radicals R on the respective carbon atom 1 to m or 1 to n, by reacting a reaction mixture comprising a lactone of the formula II

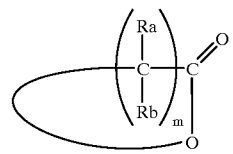

(II)

where $R^a$, $R^b$ and m are each as defined above, and a diamine of the formula III

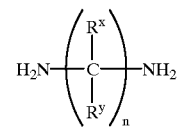

(III)

where $R^x$, $R^y$ and n are each as defined above, with elimination of water, wherein water formed by elimination is removed from the reaction mixture during the reaction.

The process of the present invention makes it possible to prepare bicyclic amidines of the formula I which have many possible uses in organic chemical synthesis, in particular in the dehydrohalogenation of organic compounds, or in polymer syntheses.

The bicyclic amidine of the formula I which can be prepared by the process of the present invention contains radicals $R^x$, $R^y$, $R^a$ and $R^b$ which can be, independently of one another, hydrogen, $C_1$–$C_{10}$-alkyl, $C_2$–$C_{10}$-alkenyl or $C_2$–$C_{10}$-alkynyl. Each of the radicals $R^x$, $R^y$, $R^a$ and $R^b$ can be, independently of one another, linear or branched or can, in each case at least pairwise, together form a ring system.

The bicyclic amidine of the formula I has two ring segments of which the first contains two nitrogen atoms and the groups $CR^xR^y$ denoted by the variable n and the second contains only one nitrogen atom (together with the fist ring segment) and the groups $CR^aR^b$ denoted by the variable m.

The lactone of the formula II has one ring containing the groups $CR^aR^b$ denoted by the variable m, which groups correspond to the groups $CR^aR^b$ of the second ring system in the bicyclic amidine.

The variables n and m are thus the number of groups $CR^aR^b$ and $CR^xR^y$, respectively, which are continuously connected to one another by C—C bonds in the respective ring or ring segment in the formulae I and II, or the number of carbon atoms $CR^xR^y$ which are continuously connected by C—C bonds between the amino groups of the diamine of the formula III.

Thus, in the case of the bicyclic amidine, the variables n and m designate the continuously connected carbon atoms denoted by the respective variable in the ring segment and index each of the carbon atoms denoted by n or m in the bicyclic amidine of the formula I with a number from 1 to n (for the carbon atoms denoted by n) or from n+1 to n+m (for the carbon atoms denoted by m).

In the case of the lactone of the formula II, the variable m designates the continuously connected carbon atoms which are denoted correspondingly in the ring and indexes each of the carbon atoms denoted by m with a number from 1 to m.

In the case of the diamine of the formula III, the variable n designates the continuously connected carbon atoms denoted correspondingly between the amino groups and indexes each of the carbon atoms denoted by n with a number from 1 to n.

The variables a, b, x and y each index the radicals R on the respective carbon atom 1 to n or 1 to m or n+1 to n+m. If, for example, n is 4, then x is 1, 3, 5 or 7, in each case corresponding to the radical $R^1$ on carbon atom 1, $R^3$ on carbon atom 2, $R^5$ on carbon atom 3 and $R^7$ on carbon atom 4. Correspondingly, y is 2, 4, 6 or 8, corresponding to the radical $R^2$ on carbon atom 1, $R^4$ on carbon atom 2, $R^6$ on carbon atom 3 and $R^8$ on carbon atom 4. The variables a and b are assigned in the same way, depending on the value of the variable m.

If, for example, m in the formula II is 3, then the formula $(-CR^aR^b)_m-$ corresponds to the radical $-CR^1R^2-CR^3R^4-CR^5R^6-$, if m is 5, then the formula $(-CR^aR^b)_m-$ corresponds to the radical $-CR^1R^2-CR^3R^4-CR^5R^6-CR^7R^8-CR^9R^{10}-$. The radicals $R^1$ to $R^{10}$ here correspond to the above definition of $R^a$ and $R^b$. An analogous situation applies to the radicals $R^x$ and $R^y$. For example, if n in the formula III is 3, then the formula $(-CR^xR^y)_n-$ corresponds to the radical $-CR^1R^2-CR^3R^4-CR^5R^6-$.

In a compound of the formula I or IV, if, for example, n is 3 and m is 3, then the formula $(-CR^xR^y)_n-$ corresponds to the radical $-CR^1R^2-CR^3R^4-CR^5R^6-$ and the formula $(-CR^aR^b)_m-$ corresponds to the radical $-CR^7R^8-CR^9R^{10}-CR^{11}R^{12}-$. Thus, the radicals are each assigned unambiguously.

For the purposes of the present invention, it is preferred that n is from 2 to 6 and m is from 3 to 7. It is particularly preferred that n is from 2 to 4 and m is from 3 to 5; in a very particularly preferred embodiment, n is 3.

It is likewise preferred for the purposes of the present invention that the radicals $R^x$, $R^y$, $R^a$ and $R^b$ are, independently of one another, hydrogen, hydroxyl or $C_1$–$C_4$-alkyl; it is particularly preferred that all radicals $R^x$, $R^y$, $R^a$ and $R^b$ are hydrogen.

The bicyclic amidines of the formula I are prepared by means of a reaction mixture comprising a lactone of the formula II.

Since the lactone is converted into part of the bicyclic amidine, the radicals $R^a$ and $R^b$ present in the lactone correspond to the respective radicals present in the desired bicyclic amidine. Accordingly, it is preferred that $R^a$ and $R^b$ are, independently of one another, hydrogen, hydroxyl, amino or $C_1$–$C_4$-alkyl, in particular hydrogen. Correspondingly, the variable m is preferably 3–8, in particular 3.

For the purposes of the present invention, preferred lactones of the formula II are γ-butyrolactone, γ- or δ-valerolactone, γ-, δ- or ε-caprolactone or other substituted lactones, for example pantolactone (2-hydroxy-3,3-dimethylbutyrolactone).

As a further component, the reaction mixture used in the process of the present invention for preparing bicyclic amidines comprises a diamine of the formula III.

Since the diamine also becomes part of the bicyclic amidine, the radicals $R^x$ and $R^y$ correspond to the radicals present in the desired bicyclic amidine of the formula I. $R^x$ and $R^y$ are preferably, independently of one another, hydrogen or $C_1$–$C_4$-alkyl, in particular hydrogen.

The variables x and y each index the radicals R on the respective carbon atom 1 to n. Indexing is therefore as described in the above example for the variables a and b.

Suitable diamines of the formula III are, for example, 1,2-diaminoethane, 1,2-diaminopropane or 1,3-diaminopropane, 1,3-diaminobutane, 1,4-diaminobutane, 1,2-diaminocyclohexane, 2,n-diaminoalkanes such as 2,3-diaminobutane or branched diamines whose amino groups are separated by from 2 to about 8, in particular from 2 to 4, carbon atoms. Particular preference is given to 1,2-diaminoethane and 1,3-diaminopropane.

At the beginning of the reaction, the initial value of the molar ratio of lactones to diamines is about 1 or is less than 1; the initial ratio of lactone to diamine is preferably at least 1:1.5. There does not necessarily have to be an upper limit to the proportion of diamine, i.e. a lower limit to the lactone:diamine ratio. However, out of fundamental considerations, it may be useful to limit the amount of diamine used in relation to the lactone, i.e. to adhere, for example, to a maximum lactone:diamine ratio of 1:20, 1:10, 1:8, 1:4, 1:3 or 1:2.

In the process of the present invention, water formed by elimination is removed from the reaction mixture during the reaction. It is advantageous if the removal of the water is carried out not only at a single, particular point during the course of the reaction, but at two or more successive points in time, for example at equal time intervals, during the course of the reaction. It is likewise possible for the water formed by elimination to be removed continuously over a period which corresponds to at least half of the total reaction time.

In a particularly preferred embodiment of the process of the present invention, the water is removed continuously from the reaction mixture over the total reaction time.

The water can be removed from the reaction mixture by the customary methods employed in organic chemical synthesis. In particular, the water is removed from the reaction mixture by distillation, in which case it is advantageous if the reaction mixture comprises at least one component which serves as entrainer for the water to be removed from the reaction mixture and the water formed by elimination is thus removed with the aid of an entrainer.

Suitable entrainers are all those compounds whose boiling point is sufficiently high for the entrainer to be able to be used at the temperatures prevailing in the reaction and which are inert toward the compounds I to IV. The boiling point of the entrainer should be at least 120° C., but preferably above this value. Particularly suitable entrainers are all compounds which form an azeotrope with water, e.g. liquid, polycyclic hydrocarbons such as tetralin or decalin.

However, for the purposes of the present invention the entrainer used for removing the water from the reaction mixture is particularly preferably the diamine employed for the reaction. In general, diamines are excellent entrainers for water. Therefore, in a particularly preferred embodiment of the invention, the water formed by elimination during the reaction is removed with the aid of the diamine of the formula III present in the reaction mixture.

Since this continually withdraws a diamine required for the reaction from the reaction mixture, further diamine should be fed into the reaction mixture in that amount in which it is withdrawn from the reaction by distillation. The amount of diamine fed to the reaction mixture should be at least that necessary for complete reaction of the as yet unreacted lactone of the formula II present in the reaction mixture. In other words, at any point in time there should be at least an equimolar ratio of unreacted lactone of the formula II and diamine of the formula III present in the reaction mixture.

A further criterion for the amount of diamine of the formula III fed in during the course of the reaction is that sufficient removal of the water formed in the reaction by elimination should be possible at any point in time during the reaction. Since the amount of water formed decreases during the reaction, the amount of diamine fed in can also decrease during the course of the reaction.

The reaction temperature is, depending on the reactants present in the reaction mixture, namely the lactone of the formula II and the diamine of the formula III, from about 80° C. to about 350° C., preferably from about 130° C. to 350° C. Low reaction temperatures of, for example, about 80° C., 100° C., 120° C. to about 150° C. generally lead to the desired product if a sufficiently long reaction time is provided. As a rule, it is advantageous for the reaction temperatures in the process of the present invention to be relatively high, for example 170° C., 190° C., 200° C., 210° C. or even above. Good results can be obtained, for example, in the case of lactones and diamines which react only with difficulty, for example for steric reasons or because of the decreasing entropy of ring closure, when the reaction temperature is, for example, from about 220° C. to about 300° C., in particular about 240° C. or about 250° C. In a preferred embodiment of the process of the present invention, the reaction temperature is from about 120° C. to about 220° C.

The reaction time is, depending on the reaction temperature, more than about 3 hours, for example from about 5 hours to about 100 hours, preferably for about 10 hours to about 80 hours and in particular from about 24 hours to about 60 hours.

In a preferred embodiment of the invention, the reaction is carried out at from about 180 to about 210° C. for a reaction time of from about 24 to about 72 hours, in particular about 48 hours.

Examples of bicyclic amidines which can be prepared according to the present invention are 1,5-diazabicyclo[4.3.0]non-5-ene (DBN), 1,8-diazabicyclo[5.4.0]undec-7-ene (DBU), 1,6-diazabicyclo[5.5.0]dodec-6-ene, 1,7-diazabicyclo[6.5.0]tridec-7-ene, 1,8-diazabicyclo[7.4.0]tridec-8-ene, 1,8-diazabicyclo[7.5.0]tetradec-8-ene, 1,5-diazabicyclo[4.4.0]dec-5-ene (DBD), 1,8-diazabicyclo[5.3.0]dec-7-ene, 1,10-diazabicyclo[7.3.0]dodec-9-ene, 1,10-diazabicyclo[7.4.0]tridec-9-ene or the appropriately substituted derivatives of these compounds. Particular preference is given to DBN, DBD or DBU or a mixture of two or more thereof.

A particular aspect of the process of the present invention is that it proceeds via an (isolable) intermediate in the form of a diazacycloalkene of the formula IV

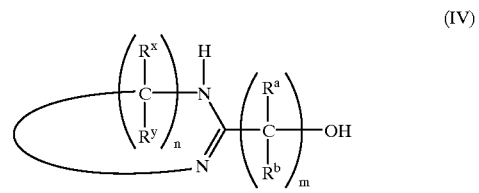

(IV)

where this intermediate can be isolated by means of a particular reaction procedure likewise disclosed below as part of the scope of the present invention. It is assumed that the formation of this intermediate having the formula IV follows the formation of an open-chain acid amide.

The radicals $R^x$, $R^y$, $R^a$ and $R^b$ are identical to the corresponding radicals in the lactone of the formula II originally used and the diamine of the formula III.

To obtain particularly high yields of bicyclic amidine of the formula I, it is therefore appropriate to continue the reaction until the intermediate of the formula IV has been essentially completely converted into the bicyclic amidine of the formula I. Therefore, a preferred embodiment of the process of the invention comprises continuing the reaction until essentially complete conversion of the intermediate of the formula IV into the desired bicyclic amidine of the formula I has taken place.

However, all intermediate stages in the reaction procedure are also conceivable in the process of the present invention. This means that the ratio of intermediate of the formula IV and bicyclic amidine of the formula I present in the reaction mixture can be controlled by varying the reaction conditions.

The process of the present invention can, by selection of an appropriate reaction time and reaction temperature, be adapted so that the diazaocycloalkene of the formula IV formed as an intermediate can be isolated in high yields.

Accordingly, the present invention also provides a process for preparing a diazacycloalkene of the formula IV, by reacting a reaction mixture comprising a lactone of the formula II and a diamine of the formula III with elimination of water, for example at a reaction temperature of from 80° C. to 350° C., wherein water formed by elimination is removed from the reaction mixture during the reaction time and the reaction is stopped at a point in time at which the diazacycloalkene of the formula IV is present in the reaction mixture.

The point in time at which the reaction is stopped is determined, for example, by the desired yield of diazacycloalkene of the formula IV. In the present case, the amount of diazacycloalkene in the reaction mixture first increases at the beginning of the reaction and decreases again as the reaction continues due to conversion of the diazacycloalkene into bicyclic amidine. A concentration profile of such a reaction sequence can be obtained, for example, by analyzing the reaction mixture at particular time intervals.

To obtain the diazacycloalkene of the present invention, it is therefore advantageous, for example, first to follow the reaction at fixed time intervals by means of a suitable analytical method in order to determine the temperature and the reaction time at which the concentration of diazacycloalkene in the reaction mixture is at a maximum. A suitable analytical method is, for example, gas chromatography. If the preparative process of the present invention is applied to a reaction mixture in which the reactivity of either the lactone or the diamine, or possibly both, in the preparative process of the present invention cannot yet be estimated, it is advisable to commence the reaction at a low temperature, for example in a temperature range of about 130–180° C., preferably a temperature range of about 150–170° C., and subsequently to analyze the reaction mixture, for example by gas chromatography, at particular time intervals, for example every two hours, every four hours or every eight hours. If the reaction rate is too low, i.e. formation of the diazacycloalkene of the formula IV is too slow, the reaction temperature, for example, can subsequently be increased, with temperature steps of, for example, 5° C. or 10° C. being advantageous. If the reaction rate is too high, i.e. the further reaction of the diazacycloalkene formed to the bicyclic amidine is too fast, the reaction temperature can, if appropriate, be reduced until the reaction rate of diazacycloalkene formation is much greater than the reaction rate of the formation of the bicyclic amidine.

In this way, when the reactivity of at least one of the two components in the reaction of lactones and diamines by the process of the present invention cannot be estimated, it is possible, in a simple manner, to obtain a reaction profile according to which new reactions can subsequently be carried out.

To obtain the novel diazacycloalkene of the formula IV, the reaction can, in principle, be stopped at any point in time at which the diazacycloalkene is present in the reaction mixture. However, this is generally done at a point in time at which the amount of diazacycloalkene present in the reaction mixture is as great as possible, i.e. when the amount of diazacycloalkene formed during the reaction is at a maximum or at least close to this maximum. In cases where a product mixture comprising not only the diazacycloalkene but also further products formed during the reaction, e.g. an open-chain amide or the bicyclic amidine of the formula I, is desired, the reaction can be stopped at a point in time at which the desired products are present in the reaction mixture in the desired ratio. The ratio of the products in the reaction mixture can be determined by suitable analytical methods, for example by gas chromatography.

The conditions applicable to the preparation of the diazacycloalkene of the formula IV are essentially the same as those for the preparation of the bicyclic amidine of the formula I, except for reaction temperature and reaction time which generally have to be varied from the values in the preparative process for the bicyclic amidine. The temperature at which the diazacycloalkene is predominantly formed but further reaction to the bicyclic amidine does not yet take place or takes place only to a subordinate extent can vary as a function of the lactone of the formula II which is used and of the diamine of the formula III which is used. A fundamental guide here is that the reaction temperature required for preparing the diazacycloalkene of the formula IV drops with increasing stability of the diazacycloalkene formed while a higher temperature has to be employed as the steric hindrance in the formation of the diazaocycloalkene increases. As a rule, higher temperatures favor the further reaction to the bicyclic amidine, while lower temperatures mean a slower reaction but lead to the diazacycloalkene with greater selectivity and very largely avoid a further reaction to form the bicyclic amidine.

If, for example, unsubstituted lactones are reacted with unsubstituted diamines, the reaction temperature is advantageously selected in the range from about 61° C. to about 200° C., for example 80° C., 100° C., 120° C., 130° C, 150° C., 160° C., 170° C., 180° C. or 190° C., with reaction times from about 8 hours about 24 hours being advantageous.

In a further embodiment of the invention, both in the preparation of the bicyclic amidine and in the preparation of the diazacycloalkene, the reaction temperature is increased during the reaction. This can be particularly useful when the reaction is to be carried out under particularly mild conditions to give high yields of the diazacycloalkene, with acceptance of longer reaction times. Thus, for example, the overall reaction time can be divided into from 2 to about 6 phases, preferably about 3 or 4 phases, in which the reaction temperature is in each case increased by about 2° C.–30° C., in particular about 5° C.–15° C.

The process of the present invention for preparing the bicyclic amidines of the formula I and the process of the invention for preparing the diazacycloalkenes of the formula IV are generally carried out at a pressure of from about 0.1 to about 1.5 bar. However, the reaction is preferably carried out without application of pressure, i.e. at ambient pressure or under a slightly reduced pressure.

The present invention further provides a diazacycloalkene of the formula IV

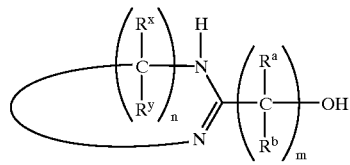

(IV)

where $R^a$, $R^b$, $R^x$, $R^y$, n and m are as defined above.

The invention likewise provides for a method for preparing bicyclic amidines of the formula I, wherein a diazacycloalkene of the formula IV is used.

The invention is illustrated by the examples.

EXAMPLES

Example 1

DBN 489 g (6.6 mol) of 1,3-diaminopropane (DAP) were placed in a 1 l flask provided with magnetic stirrer, dropping funnel, heating bath and a 100 cm column (packed with V2A rings) and brought to the boiling point (135° C.). At an internal temperature of not more than 190° C., 353.6 g, (4.11 mol) of γ-butyrolactone were added dropwise (molar ratio= 1:1.6). Subsequently, while distilling, fresh diaminopropane was fed in to keep the molar ratio approximately constant (see Table 1). In this way, the water formed in the reaction was distilled off using the DAP as entrainer.

TABLE 1

| Temp. [° C.] | Temp. of the liquid in the flask [° C.] | Fresh DAP [g] | Dis- tillate [g] | H₂O in dis- tillate (*) | A- mide a) [% by area] | Dch (**),a) [% by area] | DBN a) [% by area] |
|---|---|---|---|---|---|---|---|
| 125 | 190 | 216 | 375 | 56 | 80 | 18 | 2 |
| 130 | 200 | 170 | 192 | 68 | 30 | 60 | 10 |
| 135 | 210 | 175 | 229 | 70 | 10 | 20 | 70 |

(*) [mol % of theory]
(**) Diazacyclohexene
a) GC analysis of the mixture in the flask The synthesis was stopped and the crude product was distilled via a 20 cm Vigreux column. This gave 228 g of DBN having a purity of >97%.

The identity of the intermediate 2-(3-hydroxypropyl)-1,3-diazacyclohex-1-ene was confirmed by NMR analysis after recrystallization:

$^1$H-NMR: m (4H), 1.7–1.9 ppm, t (2H) 2.21 ppm, m (4H), 3.22 ppm, t (2H) 3.60 ppm, s (1H, br.) 6.25 ppm, s (1H) 7.63 ppm $^{13}$C-NMR: 20.4 ppm, 30.1 ppm, 33.1 ppm, 41.1 ppm, 61.2 ppm, 159.8 ppm. Melting point: 96° C., tertiary amine number: 368 (93% of theory), OH number: 387 (98% of theory)

Example 2

DBN

Using a method similar to Example 1, 25.4 mol of butyrolactone were reacted with 35 mol of 1,3-DAP (molar ratio=1.38). After a reaction time of 32 hours, the temperature of the liquid in the flask was 220° C. and 73% of the theoretically possible amount of water had been distilled off. Distillation gave 12 mol of DBN having a purity of more than 99.1%. The total yield of DBN, including the amount still present in the distillation residues, was 83.3%.

Example 3

2-(4-Hydroxybutyl)-1,3-diazacyclohex-1-ene

Using a method similar to Example 1, valerolactone was reacted with 1,3-DAP. At a temperature of 170° C. in the liquid in the flask, 48% of the open-chain amide and 49% of 2-(4-hydroxybutyl)-1,3-diazacyclohex-1-ene were obtained after 8 hours. After a further 8 hours at 180° C. and 8 hours at a liquid-phase temperature of 190° C., the ratio shifted further to 5% of amide and 92% of 2-(4-hydroxybutyl)-1,3-diazacyclohex-1-ene. The subsequent product diazabicyclodecene was obtained in an amount of only 1 or 3%.

The identity of the 2-(4-hydroxybutyl)-1,3-diazacyclohex-1-ene was confirmed by NMR analysis after recrystallization:

$^1$H-NMR: m (2H) 1.55 ppm, m (2H) 1.63 ppm, m (2H) 1.75 ppm, t (2H) 2.12 ppm, m (4H) 3.30 ppm, t (2H) 3.59 ppm, s (1H, br.) 5.65 ppm, s (1H) 7.47 ppm $^{13}$C-NMR: 20.4 ppm, 23.6 ppm, 31.8 ppm, 35.3 ppm, 41.1 ppm, 61.0 ppm, 159.7 ppm Tertiary amine number: 342 (95% of theory), OH number: 35 1 (98% of theory).

Example 4

2-(4-Hydroxypentyl)-1,3-diazacyclohex-1-ene

Using a method similar to Example 1, caprolactone was reacted with 1,3-DAP. At a temperature of 170° C. in the liquid in the flask, 89% of the open-chain amide and 10% of 2-(4-hydroxypentyl)-1,3-diazacyclohex-1-ene were obtained after 8 hours. After a further 8 hours at 180° C. and 8 hours at a liquid-phase temperature of 190° C., the ratio shifted further to 8% of amide and 89% of 2-(4-hydroxypentyl)-1,3-diazacyclohex-1-ene. The subsequent product diazabicycloundecene (DBU) was obtained in an amount of only 1 or 3%.

The identity of the 2-(4-hydroxypentyl)-1,3-diazacyclohex-1-ene was confirmed by GC/MS and NMR analysis after recrystallization (the product still contained small amounts of impurities):

$^1$H-NMR: m (2H) 1.35 ppm, m (4H) 1.55 ppm, m (2H) 1.75 ppm, t (2H) 2.08 ppm, m (4H) 3.26 ppm, t (2H) 3.58 ppm, s (1H, br.) 4.82 ppm, s (1H) 7.41 ppm $^{13}$C-NMR: 20.5 ppm, 25.5 ppm, 27.1 ppm, 32.2 ppm, 36.2 p)pm, 41.3 ppm, 61.8 ppm, 156.6 ppm.

We claim:

1. A process for preparing a bicyclic amidine of the formula I

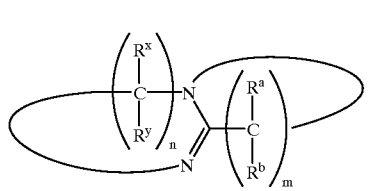

(I)

where $R^x$, $R^y$, $R^a$ and $R^b$ are each, independently of one another, hydrogen, or $C_1$–$C_{10}$-alkyl, $C_2$–$C_{10}$-alkenyl, $C_2$–$C_{10}$-alkynyl or $C_6$–$C_{12}$-aryl, groups where the groups can in turn be further substituted by hydroxy, amino, $C_1$–$C_4$-alkylamino or mercapto substituents, and n and m are, independently of one another, numbers from 2 to 12, where a, b, x and y each index the groups R on the respective carbon atom 1 to m or 1 to n, by reacting a reaction mixture comprising a lactone of the formula II

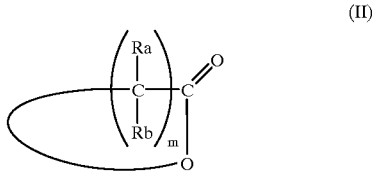

(II)

where $R^a$, $R^b$ and m are each as defined above, and a diamine of the formula III

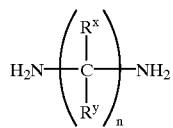
(III)

where $R^x$, $R^y$ and n are each as defined above,
with elimination of water, wherein water formed by elimination is removed from the reaction mixture during the reaction.

2. A process as defined in claim 1, wherein a diazacycloalkene of the formula IV

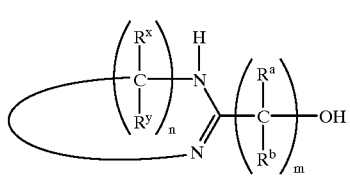
(IV)

where $R^x$, $R^y$, $R^a$ and $R^b$ are as defined in claim 1, is formed as an intermediate and the reaction is continued until essentially complete conversion of the intermediate into the bicyclic amidine of the formula I has taken place.

3. A process as defined in claim 1, wherein the water formed by elimination is removed over a period of time which corresponds to at least half the total reaction time.

4. A process as defined in claim 1, wherein the water formed by elimination is removed with the aid of an entrainer.

5. A process as defined in claim 1, wherein at least one diamine of the formula III is fed into the reaction mixture during the reaction.

6. A process as defined in claim 1, wherein one or more of the following process parameters is/are adhered to:
   a) the reaction temperature is from 170° C. to 220° C.,
   b) the reaction time is from 5 hours to 100 hours,
   c) the water is removed continuously from the reaction mixture during the entire reaction time,
   d) the reaction is carried out at a pressure of from 0.1 to 1.5 bar, preferably at ambient pressure.

7. A method for preparing a bicyclic amidine of the formula I as defined in claim 1, wherein a diazacycloalkene of the formula IV is used.

8. A process as defined in claim 1 wherein 1,5-diazabicyclo(4.3.0)none-5-ene is prepared by reacting y-butyrolactone with 1,3-diaminopropane.

* * * * *